United States Patent
Tay et al.

(10) Patent No.: US 12,346,793 B2
(45) Date of Patent: Jul. 1, 2025

(54) SORTING ATTENTION NEURAL NETWORKS

(71) Applicant: Google LLC, Mountain View, CA (US)

(72) Inventors: Yi Tay, Santa Clara, CA (US); Liu Yang, Sunnyvale, CA (US); Donald Arthur Metzler, Jr., Marina del Rey, CA (US); Dara Bahri, Lafayette, CA (US); Da-Cheng Juan, Sunnyvale, CA (US)

(73) Assignee: Google LLC, Mountain View, CA (US)

( * ) Notice: Subject to any disclaimer, the term of this patent is extended or adjusted under 35 U.S.C. 154(b) by 1092 days.

(21) Appl. No.: 17/169,718

(22) Filed: Feb. 8, 2021

(65) Prior Publication Data

US 2021/0248450 A1 Aug. 12, 2021

Related U.S. Application Data

(60) Provisional application No. 62/971,852, filed on Feb. 7, 2020.

(51) Int. Cl.
*G06N 20/00* (2019.01)
*G06F 17/16* (2006.01)
*G06N 3/047* (2023.01)

(52) U.S. Cl.
CPC ............ *G06N 3/047* (2023.01); *G06F 17/16* (2013.01); *G06N 20/00* (2019.01)

(58) Field of Classification Search
CPC ......... G06N 3/047; G06N 20/00; G06F 17/16
See application file for complete search history.

(56) References Cited

U.S. PATENT DOCUMENTS

| | | | |
|---|---|---|---|
| 5,822,742 A * | 10/1998 | Alkon | G06N 3/04 706/31 |
| 10,853,725 B2 * | 12/2020 | Chrzanowski | G06N 3/044 |
| 11,410,015 B1 * | 8/2022 | Naumov | G06N 7/01 |
| 2018/0198602 A1 * | 7/2018 | Duffy | G06F 40/117 |
| 2018/0341860 A1 * | 11/2018 | Shazeer | G06N 20/00 |
| 2019/0073580 A1 * | 3/2019 | Dzhulgakov | G06N 3/045 |
| 2019/0073586 A1 * | 3/2019 | Chen | G06N 3/084 |
| 2020/0372660 A1 * | 11/2020 | Li | G06V 10/764 |

OTHER PUBLICATIONS

Cheonbok Park, etc., "SANVis: Visual Analytics for Understanding Self-Attention Networks", published in ARXIV at id 1909.09595 on Sep. 13, 2019, retrieved May 28, 2024. (Year: 2019).*

(Continued)

*Primary Examiner* — Shourjo Dasgupta
(74) *Attorney, Agent, or Firm* — Fish & Richardson P.C.

(57) ABSTRACT

A system for performing a machine learning task on a network input is described. The system includes one or more computers and one or more storage devices storing instructions that, when executed by the one or more computers, cause the one or more computers to implement (i) multiple sorting networks in which each sorting network is configured to sort vector blocks in a sequence of vector blocks to generate a sorted sequence of vector blocks; and (ii) a sorting attention neural network configured to perform the machine learning task on the input sequence by executing multiple sorting attention mechanisms using the sorting networks.

20 Claims, 3 Drawing Sheets

(56) References Cited

OTHER PUBLICATIONS

Alexey Dosovitskiy, etc., "You Only Train Once: Loss-Conditional Training of Deep Networks", published Dec. 19, 2019 via ICLR 2020 Conference Blind Submission, retrieved May 28, 2024. (Year: 2019).*
Hyeonwoo Noh, etc., "Regularizing Deep Neural Networks by Noise: Its Interpretation and Optimization", published Oct. 14, 2017 via 31st Conference on Neural Information Processing Systems, Long Beach, CA, USA (2017), retrieved May 28, 2024. (Year: 2017).*
Ranjit, "Attention in RNN", published Aug. 13, 2019 to https://medium.com/@ranjit.aec/attentation-in-rnn-and-cnn-82f9f7cc7db1, retrieved May 28, 2024. (Year: 2019).*
Cody Marie Wild, "Conditional Love: The Rise of Renormalization Techniques for Conditioning Neural Networks", published Sep. 8, 2019 at https://towardsdatascience.com/conditional-love-the-rise-of-renormalization-techniques-for-neural-network-conditioning-14350cb10a34, retrieved May 28, 2024. (Year: 2019).*
Juho Lee, etc., "Set Transformer: A Framework for Attention-based Permutation-Invariant Neural Network", published via the Proceedings of the 36th International Conference on Machine Learning, Long Beach, CA, USA (2019), retrieved May 28, 2024. (Year: 2019).*
Nghi D.Q. Bui, etc., "AutoFocus: Interpreting Attentio-Based Neural Networks by Code Perturbation", published via 2019 34th IEEE/ACM International Conference on Automated Software Engineering (ASE), San Diego, CA, USA (2019), retrieved May 28, 2024. (Year: 2019).*
Beyrem Khalfaoui, etc., "Adaptive structured noise injection for shallow and deep neural networks", published in ARXIV at id 1909.09819v1 on Sep. 21, 2019, retrieved May 28, 2024. (Year: 2019).*
Jason Brownlee, "Train Neural Networks with Noise to Reduce Overfitting", published on Aug. 6, 2019 to https://machinelearningmastery.com/train-neural-networks-with-noise-to-reduce-overfitting/, retrieved May 28, 2024. (Year: 2019).*
Roger Grosse and Jimmy Ba, "CSC421/2516 Lecture 16: Attention", published Mar. 12, 2019 to https://www.cs.toronto.edu/~rgrosse/courses/csc421_2019/slides/lec16.pdf, retrieved May 29, 2024 (Year: 2019).*
Yi Tay, etc., "Compositional De-Attention Networks", published via 33rd Conference on Neural Information Processing Systems (NeurIPS 2019), Vancouver, Canada, 2019, retrieved Nov. 22, 2024. (Year: 2019).*
Rewon Child, etc., "Generating Long Sequences with Sparse Transformers", published to arXiv as of Apr. 23, 2019, retrieved Feb. 21, 2025. (Year: 2019).*
Adams et al., "Ranking via sinkhorn propagation" arXiv, 2011, 12 pages.
Baevski et al, "Adaptive input representations for neural language modeling" arXiv, 2018, 12 pages.
Bowman et al, "A large annotated corpus for learning natural language inference" arXiv, 2015, 11 pages.
Chelba et al, "One billion word benchmark for measuring progress in statistical language modeling" arXiv, 2013, 6 pages.
Child et al, "Generating long sequences with sparse transformers" arXiv, 2019, 20 pages.
Dai et al, "Transformer-XL: Attentive language models beyond a fixed-length context" arXiv, 2019, 20 pages.
Guo et al, "Star-transformer" arXiv, 2019, 11 pages.
Jang et al, "Categorical reprameterization with gumbel-softmax" arXiv, 2016, 12 pages.
Kitarv et al, "Reformer: The efficient transformer" International Conference on Learning Representations, 2020, 11 pages.
Luong et al, "Effective approaches to attention-based neural machine translation" arXiv, 2015, 11 pages.
Maas et al, "Learning word vectors for sentiment analysis" Proceedings of the 49th annual meeting of the association for computational linguistics, 2011, 9 pages.
Martins et al, "From softmax to sparsemax: A sparse model of attention and multi-label classification" International Conference on Machine Learning, 2016, 10 pages.
Mena et al, "Learning latent permutations with gumbel-sinkhorn networks" arXiv, 2018, 22 pages.
Vaswani et al, "Attention is all you need" NIPS, 2017, 15 pages.
Vaswani et al, "Tensor2Tensor for neural machine translation" arXiv, 2018, 9 pages.
Williams et al, "A broad-coverage challenge corpus for sentence understanding through inference" arXiv, 2017, 11 pages.
Xu et al, "Show, attend, and tell: Neural image caption generation with visual attention" International Conference on Machine Learning, 2015, 22 pages.
Parmar et al, "Image transformer" arXiv, 2018, 10 pages.
Qui et al, "Blockwise self-attention for long document understanding" ICLR, 2020, 13 pages.
Rae et al., "Compressive transformers for long-range sequence modelling" International Conference on Learning Representations, 2020, 19 pages.
Shazeer et al, "Outrageously large neural networks: The sparsely-gated mixture-of-experts layer" arrXiv, 2017, 19 pages.
Shazeer et al, "Mesh-tensorflow: Deep learning for supercomputers" NIPS, 2018, 10 pages.
Shen et al, "Reinforced self-attention network: a hybrid of hard and soft attention for sequence modeling" arXiv, 2018, 9 pages.
Shen et al, "Bi-directional block self-attention for fast and memory-efficient sequence modeling" arXiv, 2018, 18 pages.
Sinkhorn, "A relationship between arbitrary positive matrices and doubly stochastic matrices" The Annals of Mathematical Statistics, 1964, 4 pages.
So et al, "The evolved transformer" arXiv, 2019, 14 pages.
Socher et al, "Recursive deep models for semantic compositionality over a sentiment treebank" Proceedings of 2013 conference on empirical methods in natural language processing, 2013, 12 pages.
Sutskever et al., "Sequence to sequence learning with neural networks" arXiv, 2014, 9 pages.
Tay et al, "Simple and errective curriculum pointer-generator networks for reading comprehension over long narratives" arXiv, 2019, 10 pages.
Devlin et al., "BERT: Pre-Training of Deep Bidirectional Transformers for Language Understanding," Paper, Presented at proceedings of the 2019 conference of the North American Chapter of the Association for Computational Linguistics: Human Language Technologies, Minneapolis, MN, Jun. 2-7, 2019, pp. 4171-4186.

* cited by examiner

SORTING ATTENTION NEURAL NETWORKS

CROSS REFERENCE TO RELATED APPLICATIONS

This application is a non-provisional of and claims priority to U.S. Provisional Patent Application No. 62/971,852, filed on Feb. 7, 2020, the entire contents of which are hereby incorporated by reference.

BACKGROUND

This specification relates to performing a machine learning task on a network input using neural networks.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes a system implemented as computer programs on one or more computers in one or more locations that performs a machine learning task on a network input. The network input can be a sequence or a single tensor. The machine learning task can be, for example but not limited to, reinforcement learning task, sequence to sequence sorting, language modeling, document classification, pixel-wise image generation, machine translation, speech recognition, image captioning, text to speech conversion, or natural language inference.

The subject matter described in this specification can be implemented in particular embodiments so as to realize one or more of the following advantages. The techniques described in this specification allow a neural network system to process input sequences, generate output sequences, or both more efficiently than existing attention-based networks by using a new sorting attention mechanism that is based on a dynamic, learnable sorting of internal representations of the input sequences. In particular, the described sorting attention mechanism (also referred to as Sparse Sinkhorn Attention) incorporates a sorting network that learns to partition an input sequence of length l into a sequence of $N_B$ blocks and sort these blocks. Given the sorted sequence of blocks, the system can compute quasi-global attention with only local windows, thus substantially reducing attention computation and improving memory efficiency relative to conventional attention modules. Further, the use of the sorting attention mechanism reduces memory complexity of dot-product attention while outperforming or remaining competitive to state-of-the-art attentions on a multitude of applications. In particular, the described techniques can reduce the memory complexity from $O(l^2)$ to $O(B^2+N^2)$ where $B=l/N_B$. When l is large, this factorization of sequence length brings about substantial savings in terms of memory complexity.

Thus, the described neural network system consumes fewer computational resources during inference and training than existing approaches. This makes the resulting neural networks easier to fit, i.e., easier to store and execute, on hardware devices, e.g., on mobile devices, that have limitations on a neural network layer size or on a number of neural network parameters.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a neural network system implemented as computer programs on one or more computers in one or more locations that processes a network input to generate a network output to perform a machine learning task. At least one of the network input or the network output is a sequence. For example, the network input can be a sequence or a single tensor. Similarly, the network output can be a sequence or a single tensor.

The machine learning task can be, for example but not limited to, a reinforcement learning task, sequence to sequence sorting, language modeling, document classification, pixel-wise image generation, machine translation, speech recognition, image captioning, text to speech conversion, or natural language inference.

For example, the system may be a neural machine translation system. That is, if the network input is a sequence of words in an original language, e.g., a sentence or phrase, a target network output may be a translation of the input sequence into a target language, i.e., a sequence of words in the target language that represents the sequence of words in the original language.

As another example, the system may be a speech recognition system. That is, if the network input is a sequence of audio data representing a spoken utterance, the target network output may be a sequence of graphemes, characters, or words that represents the utterance, i.e., is a transcription of the input sequence.

As another example, the system may be a natural language processing system. For example, if the network input is a sequence of words in an original language, e.g., a sentence or phrase, the target network output may be a summary of the input sequence in the original language, i.e., a sequence that has fewer words than the input sequence but that retains the essential meaning of the input sequence. The words in the summary can include words that are not in the original sequence. For example, the original sequence can be words from an electronic document, e.g., a news article, a blog post, an encyclopedia entry, and the summary can be title, headline, or bullet-pointed summary of the electronic document. As another example, if the network input is a sequence of words that form a question, the target network output can be a word or a sequence of words that form an answer to the question.

More generally, the task can be any natural language processing or understanding task, e.g., an entailment task, a paraphrase task, a textual similarity task, a sentiment task, a sentence completion task, a grammaticality task, and so on, that operates on a sequence of text in some natural language.

As another example, the task can be a text to speech task, where the input is text in a natural language or features of text in a natural language and the network output is a spectrogram, a waveform, or other data defining audio of the text being spoken in the natural language.

As another example, the task can be a health prediction task, where the input is a sequence derived from electronic health record data for a patient and the output is a prediction that is relevant to the future health of the patient, e.g., a predicted treatment that should be prescribed to the patient, the likelihood that an adverse health event will occur to the patient, or a predicted diagnosis for the patient.

As another example, the system may be part of an image processing system. For example, the input sequence can be an image, i.e., a sequence of color values from the image, and the output can be a sequence of text that describes the image. As another example, the input sequence can be a sequence of text or a different context and the output sequence can be an image that describes the context.

As another example, the system may be part of a computer-assisted medical diagnosis system. For example, the network input can be a sequence of data from an electronic medical record and the target network output can be a predicted treatment or a sequence of predicted treatments.

As another example, the neural network system may be a reinforcement learning system that selects actions to be performed by a reinforcement learning agent interacting with an environment. In order for the agent to interact with the environment, the system may receive an input sequence that includes a sequence of observations characterizing different states of the environment. The system may generate an output that specifies one or more actions to be performed by the agent in response to the received input sequence, i.e., in response to the last observation in the sequence. That is, the sequence of observations includes a current observation characterizing the current state of the environment and one or more historical observations characterizing past states of the environment.

In some implementations, the environment is a real-world environment and the agent is a mechanical agent interacting with the real-world environment. For example, the agent may be a robot interacting with the environment to accomplish a specific task, e.g., to locate an object of interest in the environment or to move an object of interest to a specified location in the environment or to navigate to a specified destination in the environment; or the agent may be an autonomous or semi-autonomous land or air or sea vehicle navigating through the environment.

In these implementations, the observations may include, for example, one or more of images, object position data, and sensor data to capture observations as the agent as it interacts with the environment, for example sensor data from an image, distance, or position sensor or from an actuator.

For example in the case of a robot the observations may include data characterizing the current state of the robot, e.g., one or more of: joint position, joint velocity, joint force, torque or acceleration, for example gravity-compensated torque feedback, and global or relative pose of an item held by the robot.

In the case of a robot or other mechanical agent or vehicle the observations may similarly include one or more of the position, linear or angular velocity, force, torque or acceleration, and global or relative pose of one or more parts of the agent. The observations may be defined in 1, 2 or 3 dimensions, and may be absolute and/or relative observations.

The observations may also include, for example, sensed electronic signals such as motor current or a temperature signal; and/or image or video data for example from a camera or a LIDAR sensor, e.g., data from sensors of the agent or data from sensors that are located separately from the agent in the environment.

In the case of an electronic agent the observations may include data from one or more sensors monitoring part of a plant or service facility such as current, voltage, power, temperature and other sensors and/or electronic signals representing the functioning of electronic and/or mechanical items of equipment.

In these implementations, the actions may be control inputs to control the robot, e.g., torques for the joints of the robot or higher-level control commands, or the autonomous or semi-autonomous land or air or sea vehicle, e.g., torques to the control surface or other control elements of the vehicle or higher-level control commands.

In other words, the actions can include for example, position, velocity, or force/torque/acceleration data for one or more joints of a robot or parts of another mechanical agent. Action data may additionally or alternatively include electronic control data such as motor control data, or more generally data for controlling one or more electronic devices within the environment the control of which has an effect on the observed state of the environment. For example in the case of an autonomous or semi-autonomous land or air or sea vehicle the actions may include actions to control navigation such as steering, and movement, e.g. braking and/or acceleration of the vehicle.

In some implementations the environment is a simulated environment and the agent is implemented as one or more computers interacting with the simulated environment. Training an agent in a simulated environment may enable the agent to learn from large amounts of simulated training data while avoiding risks associated with training the agent in a real world environment, e.g., damage to the agent due to performing poorly chosen actions. An agent trained in a simulated environment may thereafter be deployed in a real-world environment.

For example the simulated environment may be a simulation of a robot or vehicle and the reinforcement learning system may be trained on the simulation. For example, the simulated environment may be a motion simulation environment, e.g., a driving simulation or a flight simulation, and the agent is a simulated vehicle navigating through the motion simulation. In these implementations, the actions may be control inputs to control the simulated user or simulated vehicle.

In another example, the simulated environment may be a video game and the agent may be a simulated user playing the video game.

In a further example the environment may be a chemical synthesis or a protein folding environment such that each state is a respective state of a protein chain or of one or more intermediates or precursor chemicals and the agent is a computer system for determining how to fold the protein chain or synthesize the chemical. In this example, the actions are possible folding actions for folding the protein chain or actions for assembling precursor chemicals/intermediates and the result to be achieved may include, e.g., folding the protein so that the protein is stable and so that it achieves a particular biological function or providing a valid synthetic route for the chemical. As another example, the agent may be a mechanical agent that performs or controls the protein folding actions selected by the system automatically without human interaction. The observations may include direct or indirect observations of a state of the protein and/or may be derived from simulation.

In a similar way the environment may be a drug design environment such that each state is a respective state of a potential pharma chemical drug and the agent is a computer system for determining elements of the pharma chemical drug and/or a synthetic pathway for the pharma chemical drug. The drug/synthesis may be designed based on a reward derived from a target for the drug, for example in simulation. As another example, the agent may be a mechanical agent that performs or controls synthesis of the drug.

In some applications the agent may be a static or mobile software agent i.e. a computer programs configured to operate autonomously and/or with other software agents or people to perform a task. For example the environment may be an integrated circuit routing environment and the system may be configured to learn to perform a routing task for routing interconnection lines of an integrated circuit such as an ASIC. The rewards (or costs) may then be dependent on one or more routing metrics such as an interconnect resistance, capacitance, impedance, loss, speed or propagation delay, physical line parameters such as width, thickness or geometry, and design rules. The observations may be observations of component positions and interconnections; the actions may comprise component placing actions e.g. to define a component position or orientation and/or interconnect routing actions e.g. interconnect selection and/or placement actions. The routing task may thus comprise placing components i.e. determining positions and/or orientations of components of the integrated circuit, and/or determining a routing of interconnections between the components. Once the routing task has been completed an integrated circuit, e.g. ASIC, may be fabricated according to the determined placement and/or routing. Or the environment may be a data packet communications network environment, and the agent be a router to route packets of data over the communications network based on observations of the network.

Generally, in the case of a simulated environment, the observations may include simulated versions of one or more of the previously described observations or types of observations and the actions may include simulated versions of one or more of the previously described actions or types of actions.

In some other applications the agent may control actions in a real-world environment including items of equipment, for example in a data center or grid mains power or water distribution system, or in a manufacturing plant or service facility. The observations may then relate to operation of the plant or facility. For example the observations may include observations of power or water usage by equipment, or observations of power generation or distribution control, or observations of usage of a resource or of waste production. The agent may control actions in the environment to increase efficiency, for example by reducing resource usage, and/or reduce the environmental impact of operations in the environment, for example by reducing waste. The actions may include actions controlling or imposing operating conditions on items of equipment of the plant/facility, and/or actions that result in changes to settings in the operation of the plant/facility e.g. to adjust or turn on/off components of the plant/facility.

In some further applications, the environment is a real-world environment and the agent manages distribution of tasks across computing resources e.g. on a mobile device and/or in a data center. In these implementations, the actions may include assigning tasks to particular computing resources.

As further example, the actions may include presenting advertisements, the observations may include advertisement impressions or a click-through count or rate, and the reward may characterize previous selections of items or content taken by one or more users.

In general, in the above described applications, where the environment is a simulated version of a real-world environment, once the system/method has been trained in the simulation it may afterwards be applied to the real-world environment. That is, control signals generated by the system/method may be used to control the agent to perform a task in the real-world environment in response to observations from the real-world environment. Optionally the system/method may continue training in the real-world environment based on one or more rewards from the real-world environment.

Optionally, in any of the above implementations, the observation at any given time step may include data from a previous time step that may be beneficial in characterizing the environment, e.g., the action performed at the previous time step, the reward received at the previous time step, and so on.

Figure 1:
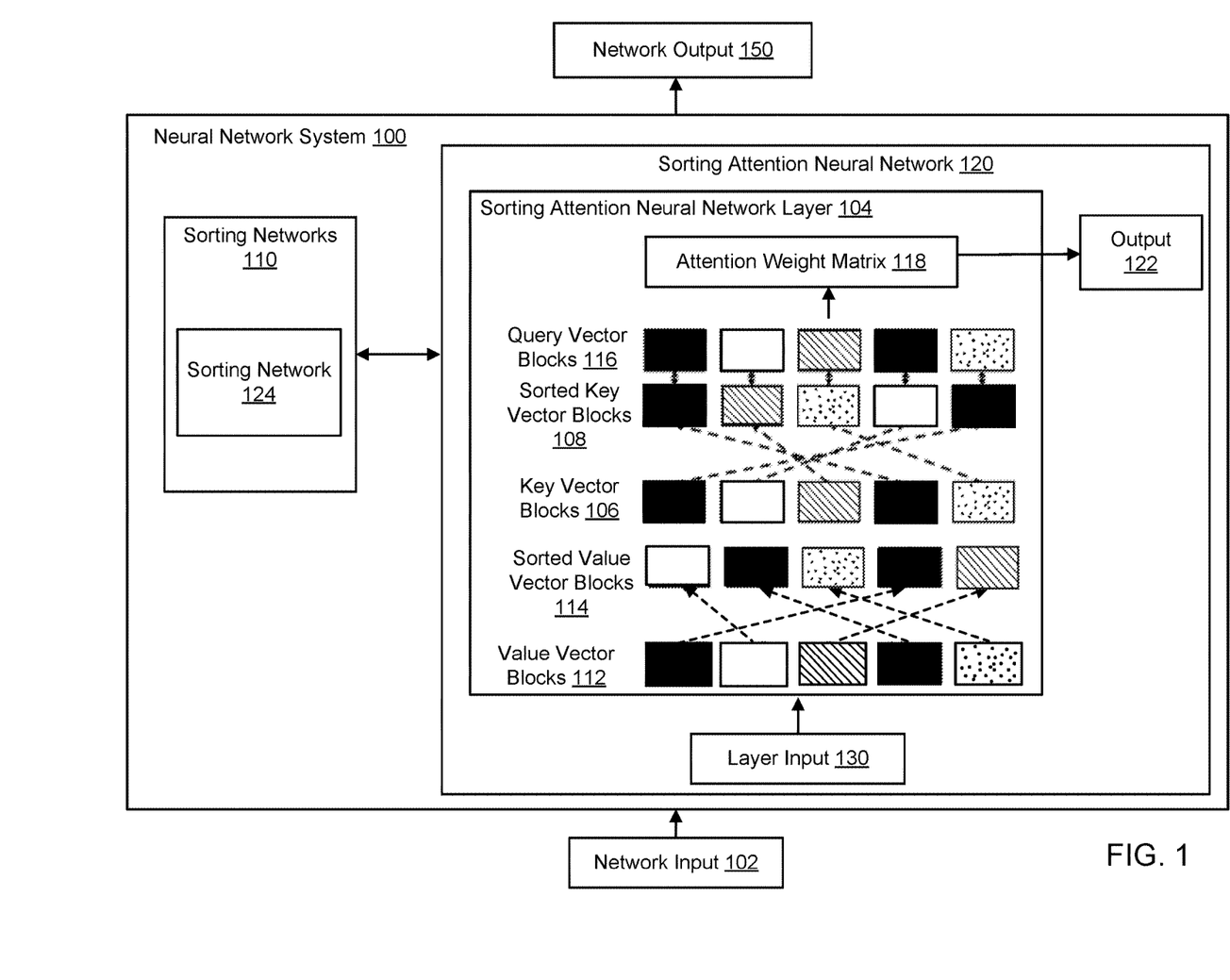
FIG. 1 shows an example neural network system that includes multiple sorting networks and a sorting attention neural network.

FIG. 1 shows an example neural network system 100 that processes a network input 102 to generate a network output 150 to perform a machine learning task. The system 100 is an example of a system implemented as computer programs on one or more computers in one or more locations, in which the systems, components, and techniques described below can be implemented.

To perform the machine learning task, the system 100 includes multiple sorting networks 110. Each of the sorting networks 110 is configured to sort vector blocks in a sequence of vector blocks to generate a sorted sequence of vector blocks. The architecture and operations of a sorting network are described in more detail below with reference to FIG. 2.

The system 100 further includes a sorting attention neural network 120 that is configured to perform the machine learning task on the network input 102 by executing multiple sorting attention mechanisms using the multiple sorting networks 110. In some implementations, two or more of the plurality of sorting attention mechanisms operate in parallel by using a multi-head attention mechanism.

In particular, the sorting attention neural network 120 includes multiple sorting attention neural network layers. While FIG. 1 illustrates one sorting attention neural network layer 104, the sorting attention neural network 120 includes a plurality of sorting attention neural network layers arranged in a stack one after the other and, optionally, other components. Each sorting attention neural network layer is configured to execute a respective sorting attention mechanism using a respective sorting network from the multiple sorting networks 110.

Generally, the layers within the sorting attention neural network 120 can be arranged in any of a variety of configurations.

As one example, when the network input of the neural network 120 is an input sequence, the sorting attention neural network 120 can include an encoder neural network that includes a subset of the plurality of sorting attention neural network layers and that encodes the input sequence to generate a respective encoded representation of each input in the sequence. In this example, the attention mechanism applied by the layers in the encoder is a self-attention mechanism, e.g., a multi-head self-attention mechanism. In a self-attention mechanism, the input vectors and the memory vectors operated on by the attention mechanism are the same, i.e., the vectors in the input sequence for the layer.

As another example, the sorting attention neural network 120 includes a decoder neural network that includes a different subset of the plurality of sorting attention neural network layers and that processes either the network input or the encoded representation of the network input to generate the network output.

In some of these examples, when the network output of the neural network 120 is an output sequence, the decoder neural network operates auto-regressively to generate the outputs in the output sequence and the attention sub-layers within some or all of the layers of the decoder apply masked self-attention over the partially generated output sequence. In masked self-attention, the input vectors and the memory vectors operated on by the attention mechanism are the same, but the attention mechanism is masked so that any given position in the input sequence does not attend over any positions after the given position in the input sequence.

When the neural network 120 includes both an encoder and a decoder, some of the layers in the decoder apply cross-attention into the encoded representations while others apply self-attention over the output sequence, either masked or not masked.

When the sorting attention neural network 120 includes a decoder neural network that operates directly on the input sequence, i.e., includes only a decoder and not an encoder, the sorting attention neural network layers within the decoder can apply a self-attention mechanism over the input sequence.

Particular examples of architectures of attention neural networks that include multiple attention layers and that can be modified to include the attention layers of the type described in this specification (e.g., the type of sorting attention layer 104) are described in Jacob Devlin, Ming-Wei Chang, Kenton Lee, and Kristina Toutanova. Bert: Pre-training of deep bidirectional transformers for language understanding. In Proceedings of the 2019 Conference of the North American Chapter of the Association for Computational Linguistics: Human Language Technologies, Volume 1 (Long and Short Papers), pp. 4171-4186, 2019; Zihang Dai, Zhilin Yang, Yiming Yang, Jaime Carbonell, Quoc Le, and Ruslan Salakhutdinov. Transformer-XL: Attentive language models beyond a fixed-length context. In Proceedings of the 57th Annual Meeting of the Association for Computational Linguistics, pp. 2978-2988, Florence, Italy, July 2019. Association for Computational Linguistics. doi: 10.18653/v1/P19-1285. URL https://www.aclweb.org/anthology/P19-1285; and Ashish Vaswani, Noam Shazeer, Niki Parmar, Jakob Uszkoreit, Llion Jones, Aidan N. Gomez, Lukasz Kaiser, and Illia Polosukhin. Attention is all you need. Advances in Neural Information Processing Systems, pp. 5998-6008, 2017. URL https://papers.nips.cc/paper/7181-attention-is-all-you-nee.pdf.

Each of the attention neural network layers in the sorting attention neural network 120 is associated with a different, respective sorting network in the multiple sorting networks 110. In some implementations, the sorting networks 110 may have the same network architecture but different network parameters.

For example, as shown in FIG. 1, the sorting attention neural network layer 104 is configured to perform a sorting attention mechanism using a respective sorting network, e.g., the sorting network 124. In particular, the sorting attention mechanism includes receiving (i) a sequence of key vector blocks 106, each key vector block including multiple key vectors, (ii) a sequence of query vector blocks 116, each query vector block including multiple query vectors, and (iii) a sequence of value vector blocks 112, each value vector block including multiple value vectors.

The sequence of key vector blocks 106, the sequence of query vector blocks 116, and the sequence of value vector blocks 112 are derived from the layer input 130, which is an input sequence including queries, keys and values. The input sequence can be partitioned, by an input embedding layer of the respective sorting network, into a sequence of vector blocks including key vector blocks, query vector blocks and value vector blocks as described in detail below with reference to FIG. 2. Depending on the position of the attention layer XXX within the sorting attention neural network 120, the layer input 130 may be embeddings from the output of a previous attention layer in the sorting attention neural network 120 or embeddings derived from the network input 102.

For example, the sorting attention neural network 120 can include an embedding neural network (e.g., an MLP network or a convolutional neural network) that generates, from the network input 102, embeddings (e.g. word embeddings in the case of language modeling or embeddings of per-timestep observations in a reinforcement learning environment) that are used as the layer input 130 by the sorting attention layer 104. As another example, the sorting attention neural network 120 may generate the embeddings as input to the sorting attention neural network layer 104 in a different way, e.g., by using a look-up table.

The queries, keys, and values can be different for different types of attention. That is, different types of attention neural network layers use different sources for the original queries, keys, and values that are received as input by the sorting attention neural network layer 104.

In particular, when the sorting attention neural network layer 104 is an encoder self-attention layer in an encoder that has multiple subnetworks, all of the keys, values and queries come from the same place, in this case, the output of the previous subnetwork in the encoder, or, for the encoder self-attention layer in the first subnetwork, the embeddings of the inputs and each position in the encoder can attend to all positions in the input order. Thus, there is a respective key, value, and query for each position in the input order.

When the sorting attention neural network layer 104 is a decoder self-attention layer in an decoder that has multiple subnetworks, each position in the decoder attends to all positions in the decoder preceding that position. Thus, all of the keys, values, and queries come from the same place, in this case, the output of the previous subnetwork in the decoder, or, for the decoder self-attention layer in the first decoder subnetwork, the embeddings of the outputs already generated. Thus, there is a respective key, value, and query for each position in the output order before the current position.

When the sorting attention neural network layer 104 is an encoder-decoder attention layer, the queries come from the previous component in the decoder and the keys and values come from the output of the encoder, i.e., from the encoded representations generated by the encoder. This allows every position in the decoder to attend over all positions in the input sequence. Thus, there is a respective query for each position in the output order before the current position and a respective key and a respective value for each position in the input order.

The sorting attention mechanism performed by the layer 104 further includes sorting the key vector blocks in the sequence of key vector blocks 106 to generate a sorted sequence of key vector blocks 108 and sorting the value vector blocks in the sequence of value vector blocks 112 to generate a sorted sequence of value vector blocks 114 using the respective sorting network 124. FIG. 1 illustrates an example of how the blocks in the sequence of value vector blocks 112 (including 5 blocks that are coded differently for illustrative purposes) are re-arranged and moved to new positions in the sequence of sorted value vector blocks 114, and how the blocks in the sequence of key vector blocks 106 are re-arranged and moved to new positions in the sequence of sorted key vector blocks 108. The process performed by the respective sorting network 124 to sort vector blocks in a sequence of vector blocks is described in detail below with respect to FIG. 2.

The sorting attention mechanism includes generating an attention weight matrix 118 based on a quasi-global attention of each query vector block in the sequence of query vector blocks 116 on a corresponding key vector block in the sorted sequence of key vector blocks 108. In some implementations, generating the attention weight matrix is further based on a local attention of each query vector block in the sequence of query vector blocks 116 on a corresponding key vector block in the sequence of key vector blocks 106.

The sorting attention mechanism includes generating an output 122 of the sorting attention mechanism based on the attention weight matrix 118 and the sorted sequence of value vector blocks 114. Generating an attention weight matrix and an output 122 is described in more detail below with reference to FIG. 3.

The output 122 of the sorting attention NN layer 104 may be provided as input to the next sorting attention neural network layer or other components of the sorting attention neural network 120 for further processing, or may be used to generate the network output 150 of the neural network system 100.

The sorting attention neural network 120 may include one or more output layers that are configured to receive the output of the final sorting attention NN layer in the sorting attention neural network 120. The one or more output layers are configured to process the output of the final sorting attention NN layer to generate the network output 150 of the neural network system 100.

In some implementations, the sorting attention neural network 120 includes a decoder neural network that includes a first subset of the multiple sorting attention mechanisms and that generates the network output 150 for the machine learning task.

In some implementations, the network output 150 is an output sequence and at least some of the sorting attention mechanisms in the first subset apply masked attention. For example, if block i is sorted into a new position p<i, then it is being masked out, i.e., the attention weight for block i is set to zero.

In some implementations, the network input 102 is an input sequence, and the sorting attention neural network includes an encoder neural network that includes a second subset of the multiple sorting attention mechanisms and that encodes the input sequence to generate a respective encoded representation of each input in the sequence.

Figure 2:
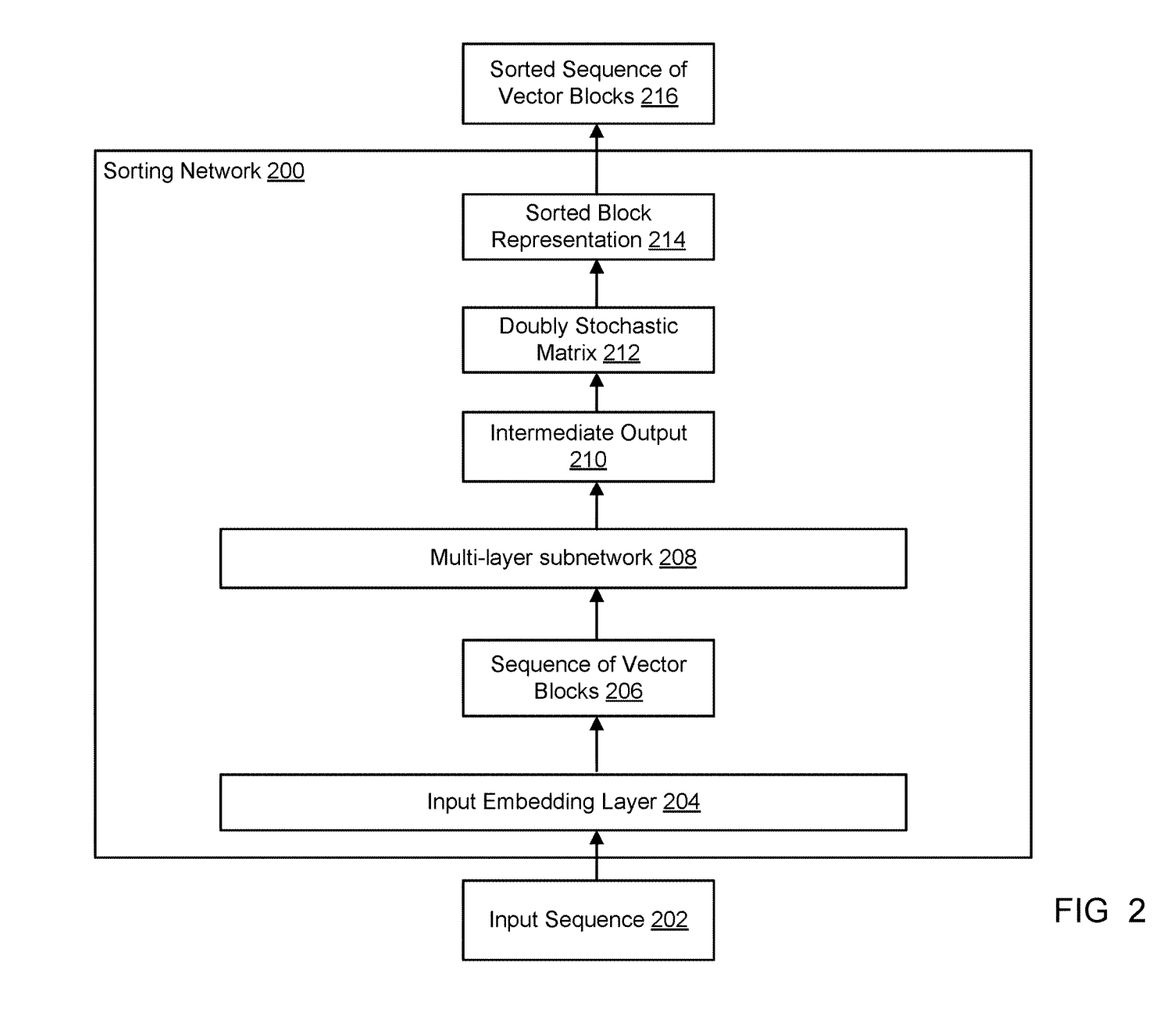
FIG. 2 shows an example architecture of a sorting network.

FIG. 2 shows an example architecture of a sorting network 200. The sorting network 200, which can be referred to as SortNet, is configured to sort vector blocks in a sequence of vector blocks to generate a sorted sequence of vector blocks. The sorting network 200 includes a multi-layer subnetwork 208 and an input embedding layer 204 preceding the multi-layer subnetwork 208. The multi-layer sub-network 208 may be a multi-layer feed-forward subnetwork with ReLU activations.

The input embedding layer 204 is configured to convert an input sequence 202 to a sequence of vector blocks 206. For example, the layer 204 receives an input sequence X of l vectors of d dimensions and converts them to (i.e., partitions them into) a block-wise representation, i.e., a sequence X' of vector blocks as follows:

$$X' = \psi_P(X) \tag{1}$$

The sequence X' includes $N_B$ blocks in which each block has a length of b tokens. The function $\psi_P(\bullet)$ is a block-wise pooling operation that maps $\mathbb{R}^{l \times d} \to \mathbb{R}^{N_B \times d}$ and $X' \in \mathbb{R}^{N_B \times d}$. In addition, the sorting network 200 adopts:

$$\psi_P(X)_i = \sum_{j=i \cdot \ell_B}^{(i+1) \cdot \ell_B} (X_j) \tag{2}$$

which is equivalent to taking the sum of embeddings of all tokens belonging to a local window (i.e., all tokens belonging to a block). $l_B$ is the length of one vector block.

The multi-layer subnetwork 208 of the sorting network 200 is configured to process the sequence of vector blocks 206 (e.g., sequence X') to generate an intermediate output 210 (denoted as R) of the multi-layer subnetwork 208 as follows:

$$R_i = P(X_i') \tag{3}$$

where i refers to the block index. $P(\bullet)$ is an arbitrary parameterized function which accepts an input vector of d dimensions and returns a vector of $N_B$ dimensions. For example, the multi-layer subnetwork 208 may parameterize P(X) using a multi-layer feed-forward subnetwork (e.g., two-layered feed-forward subnetwork) with ReLU activations as follows:

$$P(X) = \sigma(W_B \sigma(W_P(X) + b_P) + b_B) \tag{4}$$

where $W_P$ and $W_B$ are weight matrices of the multi-layer feed-forward subnetwork and $W_P \in \mathbb{R}^{d \times d}$ and $W_B \in \mathbb{R}^{d \times l_B}$. $\sigma(\bullet)$ is an activation function (e.g., a ReLU activation function), and $b_P$ and $b_B$ are bias parameters. Equation 4 allows each block to learn a projection to $N_B$ other blocks, effectively learning the position that it is supposed to be shifted (or permuted to).

The intermediate output 210, denoted as R, is also referred to as a sorting matrix. The sorting network 200 consecutively normalizes rows and columns of the sorting matrix R for $N_k$ times by performing multiple row and column normalization steps on the sorting matrix R to generate a doubly stochastic matrix 212. The doubly stochastic matrix 212 is a non-negative matrix. Each row of the doubly stochastic matrix 212 sums to 1, and each column of the doubly stochastic matrix sums to 1. The number of iterations k can be a user-defined hyperparameter. The normalization procedure is described as follows:

$$S^0(R) = \exp(R)$$

-continued $$S^k(R) = F_c(F_r(S^{k-1}(R)))$$

$$S(R) = \lim_{k \to \infty} S^k(R)(*)$$

where $F_r$, $F_c$ are the row and column wise normalization function defined as follows:

$$F_c^k(x) = F_c^{k-1}(X) \oslash (X 1_l 1_N^T)$$

$$F_r^k(x) = F_r^{k-1}(X) \oslash (1_l 1_N^T X)$$

where $\oslash$ is the element-wise division operator, N is the length of the input matrix and 1 is a vector of ones. In some implementations, the calculations can be performed in log domain for improved stability:

$$F_c^k(x) = F_c^{k-1}(X) - \log(\exp(X 1_l) 1_N^T)$$

$$F_r^k(x) = F_r^{k-1}(X) - \log(1_l 1_N^T \exp(X))$$

Equation (*) implies that iterative normalization of R converges to the doubly stochastic limit if R has support, i.e., a nonnegative matrix with a positive diagonal. The sorting matrix R is non-negative by design due to the usage of ReLU in P(X). Gradients of the iterative normalization can be computed, enabling end-to-end training of the sorting network 200.

In some implementations, the doubly stochastic matrix 212 is a permutation matrix, which has rows and columns that sum to 1 and all entries are either 0 or 1.

In some implementations where the sorting network 200 is involved in learning causal attention (e.g., no information from the future should leak to the present), to ensure that the current time steps should never have access to future time steps, at each of the plurality of row and column normalization steps, the sorting network 200 masks future information if a block of the input sequence is sorted into a new position that precedes the original position of the block. For example, if block i is sorted into a new position p<i, then it is being masked out. That means the attention weight for block i is set to zero.

In some implementations, an output of a row and column normalization step is injected with noise before being passed to the next row and column normalization step. More specifically, for S(X) to approximate the doubly stochastic permutation matrix, noise can be injected as follows:

$$S(X) = S\left(\frac{(X + \epsilon)}{\tau}\right)$$

where $\epsilon$ is the noise and $\tau$ is the temperature hyperparameter. For example, the noise can be Gumbel noise, which is described in Jang, E., Gu, S., and Poole, B. Categorical reparameterization with gumbel-softmax. arXiv preprint arXiv:1611.01144, 2016. Intuitively, lowering the temperature brings S(X) to be closer to a permutation matrix with discrete 1s and 0s.

The sorting network 200 multiplies the doubly stochastic matrix 212 (e.g., a permutation matrix) with the sequence of vector blocks 206 to generate a sorted block representation 214, and then converts the sorted block representation 214 into the sorted sequence of vector blocks 216 as follows:

$$X_S = U(RB(X)),$$

where B(•) converts an input sequence into block-wise representations, i.e., $B(X) = X' \in \mathbb{R}^{N_B \times (B \times d)}$. U(•) converts the block-wise representations back into token-wise sequences. U(•) and B(•) can be interpreted as block-wise reshaping operators. Since R is doubly stochastic, multiplying a partitioned sequence by R is equivalent to sorting it.

Figure 3:
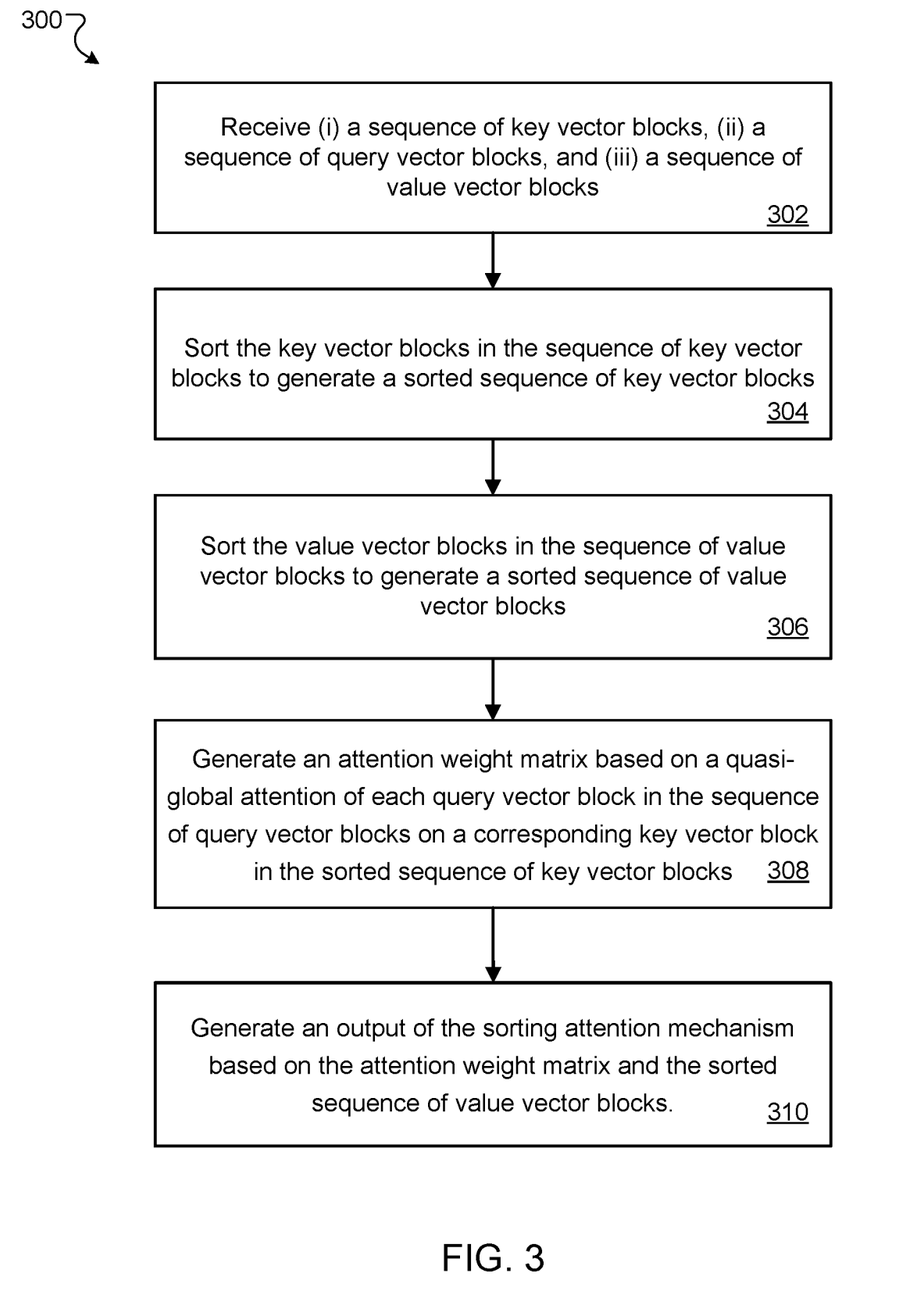
FIG. 3 is a flow diagram of an example process performed by a sorting attention mechanism.

FIG. 3 is a flow diagram of an example process 300 performed by a sorting attention mechanism. For convenience, the process 300 will be described as being performed by a system of one or more computers located in one or more locations. For example, a neural network system, e.g., the neural network system 100 of FIG. 1, appropriately programmed in accordance with this specification, can perform the process 300.

The system receives (i) a sequence of key vector blocks, each key vector block including a plurality of key vectors, (ii) a sequence of query vector blocks, each query vector block including a plurality of query vectors, and (iii) a sequence of value vector blocks, each value vector block including a plurality of value vectors (step 300).

The system sorts the key vector blocks in the sequence of key vector blocks to generate a sorted sequence of key vector blocks using a respective sorting network from multiple sorting networks (step 302).

The system sorts the value vector blocks in the sequence of value vector blocks to generate a sorted sequence of value vector blocks using the respective sorting network (step 304).

The process for sorting vector blocks in the sequence of vector blocks to generate a sorted sequence of vector blocks using the respective sorting network is described above with reference to FIG. 2.

The system generates an attention weight matrix based on a quasi-global attention of each query vector block in the sequence of query vector blocks on a corresponding key vector block in the sorted sequence of key vector blocks (step 306). In some implementations, the system generates the attention weight matrix based on a local attention of each query vector block in the sequence of query vector blocks on a corresponding key vector block in the sequence of key vector blocks.

For example, the attention weight matrix, denoted as $A_{ij}$ can be generated as follows:

$$A_{ij} = \begin{cases} (Q_i \psi_S(K)_j^\top) + Q_i(K)_j^\top, & \text{if } \lfloor j/\ell \rfloor = \lfloor i/\ell \rfloor \\ 0 & \text{otherwise} \end{cases}$$

if $\lfloor j/l \rfloor = \lfloor i/l \rfloor$ otherwise
where $\psi(\cdot)$ is the neural sorting function and $\psi_S(X) = RX'$. The above formula indicates that attention weights are only computed when $\lfloor j/l \rfloor = \lfloor i/l \rfloor$. The first term $Q_i \psi_S(K)_j^T$ is a quasi-global attention of each query vector block in the sequence of query vector blocks on a corresponding key vector block in the sorted sequence of key vector blocks $\psi_S(K)$. The secondary term $Q_i(K)_j^T$ is a local attention of each query vector block in the sequence of query vector blocks on a corresponding key vector block in the sequence of key vector blocks K.

The system generates an output Y of the sorting attention mechanism based on the attention weight matrix and the sorted sequence of value vector blocks (step 308). In particular, to generate the output Y, the system applies a softmax function on the attention weight matrix A, and multiplies the obtained result with the sorted sequence of value vector blocks $\psi_S(V)$ as follows:

$$Y = \text{Softmax}(A) \psi_S(V)$$

In some implementations, the value vector blocks are sorted in the same order as the key vector blocks, meaning that the same neural sorting function is applied to both the value vector blocks and key vector blocks to obtain a sorted sequence of value vector blocks and a sorted sequence of key vector blocks.

The system may provide the output Y of the sorting attention mechanism as input to the next sorting attention NN layer configured to perform the next sorting attention mechanism or to other components of the neural network system for further processing. If the current sorting attention NN layer performing the current sorting attention mechanism is the final layer in the sorting attention neural network, the system may provide the output Y to one or more output layers of the sorting attention neural network that are configured to map the output Y to the network output of the neural network system.

The sorting attention neural network described in this specification is trained jointly with the sorting networks on training data using conventional machine learning techniques (e.g., gradient descent with backpropagation) to optimize a common objective function that is appropriate for the machine learning task that the neural network system is configured to perform. By incorporating the sorting network that learns to partition an input sequence of length l into a sequence of $N_B$ blocks and sort these blocks, the techniques described herein allow the system to compute quasi-global attention with only local windows, thus substantially reducing attention computation and improving memory efficiency relative to conventional attention modules. Therefore, the techniques described herein allow the training of the sorting attention neural network to become much more computationally efficient and improve learning speeds (compared to the training of conventional attention neural networks having conventional attention layers).

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A system for processing a network input to generate a network output to perform a machine learning task, the system comprising one or more computers and one or more storage devices storing instructions that, when executed by the one or more computers, cause the one or more computers to implement:
   a plurality of sorting networks, each sorting network being configured to sort vector blocks in a sequence of vector blocks to generate a sorted sequence of vector blocks; and
   a sorting attention neural network configured to perform the machine learning task on the network input by executing a plurality of sorting attention mechanisms using the plurality of sorting networks, wherein each sorting attention mechanism comprises:
partitioning an input sequence into a sequence of vector blocks, wherein the input sequence is (i) an input derived from the network input or (ii) an output of a preceding sorting attention mechanism or of one or more preceding neural network layers in the sorting attention neural network,
generating, from the sequence of vector blocks, (i) a sequence of key vector blocks, each key vector block including a plurality of key vectors, (ii) a sequence of query vector blocks, each query vector block including a plurality of query vectors, and (iii) a sequence of value vector blocks, each value vector block including a plurality of value vectors;
sorting the key vector blocks in the sequence of key vector blocks to generate a sorted sequence of key vector blocks using a respective sorting network from the plurality of sorting networks;
generating an attention weight matrix based on a quasi-global attention of each query vector block in the sequence of query vector blocks on a corresponding key vector block in the sorted sequence of key vector blocks, wherein the key vector blocks within the sorted sequence of key vector blocks are in a different order from the query vector blocks within the sequence of query vector blocks; and
generating an output of the sorting attention mechanism based on the attention weight matrix,
wherein the output of each sorting attention mechanism is provided as input to the next sorting attention mechanism or to one or more subsequent neural network layers in the sorting attention neural network for further processing, and
wherein the sorting attention neural network comprises one or more output layers configured to receive a final output of a final sorting attention mechanism in the sorting attention neural network and to process the final output to generate the network output.

2. The system of claim 1, wherein the machine learning task is one of the following tasks: reinforcement learning task, sequence to sequence sorting, language modeling, document classification, pixel-wise image generation, machine translation, speech recognition, image captioning, text to speech conversion, or natural language inference.

3. The system of claim 1, wherein each of the plurality of sorting networks comprises a multi-layer subnetwork.

4. The system of claim 3, wherein the multi-layer subnetwork is a multi-layer feed-forward subnetwork with ReLU activations.

5. The system of claim 3, wherein each of the plurality of sorting networks comprises an input embedding layer preceding the multi-layer subnetwork of the sorting network.

6. The system of claim 5, wherein the input embedding layer of each of the plurality of sorting networks is configured to convert an input sequence of the respective sorting attention mechanism to a sequence of vector blocks, and wherein the multi-layer subnetwork of the sorting network is configured to process the sequence of vector blocks to generate an intermediate output of the multi-layer subnetwork.

7. The system of claim 6, wherein each of the plurality of sorting networks is further configured to:
consecutively normalize rows and columns of the intermediate output by performing a plurality of row and column normalization steps on the intermediate output to generate a doubly stochastic matrix, wherein each row of the doubly stochastic matrix sums to 1, and each column of the doubly stochastic matrix sums to 1.

8. The system of claim 7, wherein the doubly stochastic matrix is a permutation matrix.

9. The system of claim 8, wherein each of the plurality of sorting networks is configured to:
multiply the permutation matrix with the sequence of vector blocks to generate a sorted block representation, and
convert the sorted block representation to the sorted sequence of vector blocks.

10. The system of claim 7, wherein at least one of the plurality of sorting networks is configured to, at each of the plurality of row and column normalization steps, mask future information if a block of the input sequence is sorted into a new position that precedes the original position of the block.

11. The system of claim 7, wherein an output of a row and column normalization step is injected with noise before being passed to the next row and column normalization step.

12. The system of claim 1, wherein two or more of the plurality of sorting attention mechanisms operate in parallel by using a multi-head attention mechanism.

13. The system of claim 1, wherein each sorting attention mechanism comprises sorting the value vector blocks in the sequence of value vector blocks to generate a sorted sequence of value vector blocks and generating the output of the sorting attention mechanism based on the attention weight matrix and the sorted sequence of value vector blocks, wherein each sorting attention mechanism comprises truncating the sorted value vectors and the sorted key vectors before generating the attention weight matrix.

14. The system of claim 1, wherein generating the attention weight matrix is further based on a local attention of each query vector block in the sequence of query vector blocks on a corresponding key vector block in the sequence of key vector blocks.

15. The system of claim 1, wherein the plurality of sorting networks and the sorting attention neural network are jointly trained using a common objective function.

16. The system of claim 1, wherein the sorting attention neural network comprises a decoder neural network that includes a first subset of the plurality of sorting attention mechanisms and that generates a network output for the machine learning task.

17. The system of claim 16, wherein the network output is an output sequence and at least some of the sorting attention mechanisms in the first subset apply masked attention.

18. The system of claim 1, wherein the network input is an input sequence, and wherein the sorting attention neural network comprises an encoder neural network that includes a second subset of the plurality of sorting attention mechanisms and that encodes the input sequence to generate a respective encoded representation of each input in the sequence.

19. One or more non-transitory computer storage media storing instructions that, when executed by one or more computers, cause the one or more computers to perform operations comprising:
performing a machine learning task on a network input by executing a plurality of sorting attention mechanisms using a plurality of sorting networks, wherein each sorting network of the plurality of sorting networks is configured to sort vector blocks in a sequence of vector blocks to generate a sorted sequence of vector blocks, and wherein each sorting attention mechanism comprises:
  partitioning an input sequence into a sequence of vector blocks, wherein the input sequence is (i) an input derived from the network input or (ii) an output of a preceding sorting attention mechanism or of one or more preceding neural network layers in the sorting attention neural network,
  generating, from the sequence of vector blocks, (i) a sequence of key vector blocks, each key vector block including a plurality of key vectors, (ii) a sequence of query vector blocks, each query vector block including a plurality of query vectors, and (iii) a sequence of value vector blocks, each value vector block including a plurality of value vectors;
  sorting the key vector blocks in the sequence of key vector blocks to generate a sorted sequence of key vector blocks using a respective sorting network from the plurality of sorting networks;
  generating an attention weight matrix based on a quasi-global attention of each query vector block in the sequence of query vector blocks on a corresponding key vector block in the sorted sequence of key vector blocks, wherein the key vector blocks within the sorted sequence of key vector blocks are in a different order from the query vector blocks within the sequence of query vector blocks; and
  generating an output of the sorting attention mechanism based on the attention weight matrix,
wherein the output of each sorting attention mechanism is provided as input to the next sorting attention mechanism or to one or more subsequent neural network layers in the sorting attention neural network for further processing, and
wherein the operations comprises receiving a final output of a final sorting attention mechanism and processing the final output to generate a network output for the network input.

20. A computer-implemented method comprising:
performing a machine learning task on a network input by executing a plurality of sorting attention mechanisms using a plurality of sorting networks, wherein each sorting network of the plurality of sorting networks is configured to sort vector blocks in a sequence of vector blocks to generate a sorted sequence of vector blocks, and wherein each sorting attention mechanism comprises:
  partitioning an input sequence into a sequence of vector blocks, wherein the input sequence is (i) an input derived from the network input or (ii) an output of a preceding sorting attention mechanism or of one or more preceding neural network layers in the sorting attention neural network,
  generating, from the sequence of vector blocks, (i) a sequence of key vector blocks, each key vector block including a plurality of key vectors, (ii) a sequence of query vector blocks, each query vector block including a plurality of query vectors, and (iii) a sequence of value vector blocks, each value vector block including a plurality of value vectors;
  sorting the key vector blocks in the sequence of key vector blocks to generate a sorted sequence of key vector blocks using a respective sorting network from the plurality of sorting networks;
  generating an attention weight matrix based on a quasi-global attention of each query vector block in the sequence of query vector blocks on a corresponding key vector block in the sorted sequence of key vector blocks, wherein the key vector blocks within the sorted sequence of key vector blocks are in a different order from the query vector blocks within the sequence of query vector blocks; and
  generating an output of the sorting attention mechanism based on the attention weight matrix,
wherein the output of each sorting attention mechanism is provided as input to the next sorting attention mechanism or to one or more subsequent neural network layers in the sorting attention neural network for further processing, and
wherein the operations comprises receiving a final output of a final sorting attention mechanism and processing the final output to generate a network output for the network input.

* * * * *